United States Patent [19]

Stock

[11] Patent Number: 5,321,972
[45] Date of Patent: Jun. 21, 1994

[54] METHOD FOR QUANTITATIVELY DETERMINING A COMPONENT OF A GAS FLOW AND APPARATUS THEREFOR

[75] Inventor: Burkhard Stock, Lübeck, Fed. Rep. of Germany

[73] Assignee: Drägerwerk Aktiengesellschaft, Lübeck, Fed. Rep. of Germany

[21] Appl. No.: 4,503

[22] Filed: Jan. 14, 1993

[30] Foreign Application Priority Data

Jan. 15, 1992 [DE] Fed. Rep. of Germany ........ 4200830

[51] Int. Cl.⁵ ...................... G01N 33/497; G01N 1/22
[52] U.S. Cl. ..................................... 73/23.2; 73/23.3; 73/863.02; 422/84; 128/719
[58] Field of Search ............... 73/23.3, 863.02, 863.11, 73/863.61, 864.63, 23.2, 863.01, 863.03; 420/84; 128/719, 730

[56] References Cited

U.S. PATENT DOCUMENTS

| | | | |
|---|---|---|---|
| 2,795,223 | 6/1957 | Stampe | 422/84 |
| 3,764,270 | 10/1973 | Collier et al. | 73/863.02 |
| 3,854,320 | 12/1974 | Burroughs et al. | 73/23.3 |
| 4,248,245 | 2/1981 | Kempin | 73/863.02 |
| 4,297,871 | 11/1981 | Wright et al. | 73/863,02 |
| 4,300,384 | 11/1981 | Wiesner et al. | 73/863.01 |
| 4,707,336 | 11/1987 | Jones | 73/23.3 |
| 4,736,619 | 4/1988 | Legrand | 73/23.2 |
| 4,833,909 | 5/1989 | Matthiessen | 73/23.2 |
| 4,976,135 | 12/1990 | Stock | 73/23.2 |

FOREIGN PATENT DOCUMENTS 2184245 6/1987 United Kingdom ................. 422/84

Primary Examiner—Hezron E. Williams
Assistant Examiner—Michael Brock
Attorney, Agent, or Firm—Walter Ottesen

[57] ABSTRACT

The invention relates to a method for quantitatively determining a gas component of a gas flow and an apparatus therefor. The apparatus includes a testing conduit having a throttle through which the gas flow flows. A sample conduit leading to the gas inlet of a gas sensor branches away from the testing conduit upstream of the throttle. The apparatus further includes a pressure sensor connected to the sample conduit, a valve connected to a gas outlet of the gas sensor and a control unit. The method of the invention is improved in that a defined quantity of gas can be supplied to the sensor without a pump being required. An improvement is achieved in that the control unit is so configured that: in a first step, the valve is opened; the gas volume is determined in a second step by computing the time integral of the signal of the pressure sensor; and, in a third step, the valve is closed after the throughflow of a pregiven gas volume or after a pregiven time duration has elapsed.

7 Claims, 1 Drawing Sheet

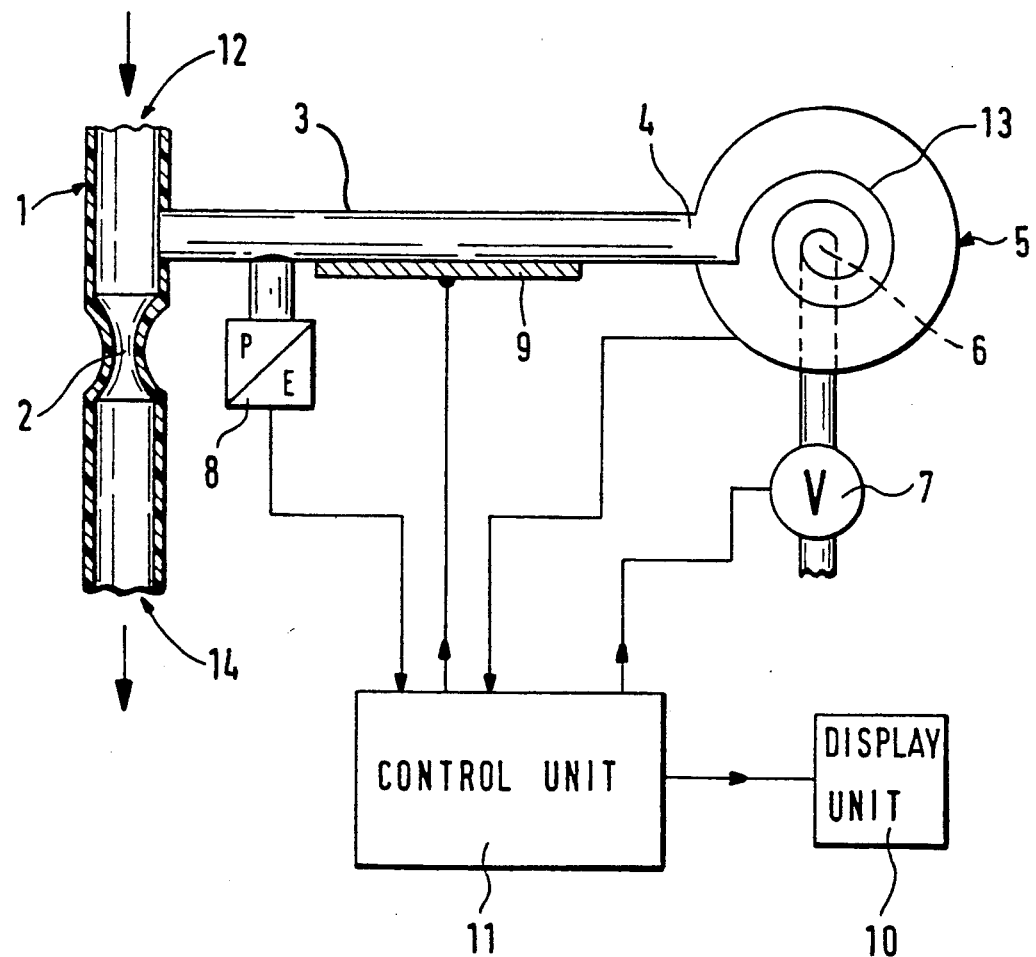

METHOD FOR QUANTITATIVELY DETERMINING A COMPONENT OF A GAS FLOW AND APPARATUS THEREFOR

BACKGROUND OF THE INVENTION

An apparatus for quantitatively determining a component of a gas flow is disclosed in U.S. Pat. No. 4,736,619. This apparatus is a breath alcohol measuring device wherein the breath is blown through a conduit into the ambient with the conduit having a restriction or throttle formed therein. A sample conduit branches off from the testing conduit upstream of the throttle and leads to an alcohol sensor. A pressure sensor is connected to the sample conduit for measuring the pressure at the throttle. The signal of the pressure sensor is integrated over time by a control unit during the time that the breath is blown into the testing tube. In this way, the air volume flowing through the testing tube into the ambient is determined. A sample-taking pump is actuated by the control unit only after so much air has flown that alveolar air is present in the testing conduit. The sample-taking pump pumps a specific quantity of air from the testing conduit through the sample conduit into the alcohol sensor. The alcohol content of the breath sample is then determined.

It is a disadvantage of this known apparatus that a sample-taking pump is necessary which, with its mechanical parts, causes the pump to be subject to failure and increases the cost of the apparatus. Furthermore, high requirements as to precision cannot be expected with a low-cost pump.

SUMMARY OF THE INVENTION

It is an object of the invention to provide a method for quantitatively determining a component of a gas flow wherein a defined quantity of gas is supplied to a sensor without the necessity of providing a pump. It is also an object of the invention to provide an apparatus for carrying out the method of the invention.

According to a feature of the invention, the control unit is so configured that: the valve is opened in a first step; the gas volume, which has flowed through the sample conduit, is determined by computing the time integral of the signal of the pressure sensor in a second step; and, the valve is closed in a third step after a pregiven gas volume has flowed through or after a pregiven time duration.

The advantage of the invention is seen in that, except for a simple open/close valve, no movable mechanical parts are required for taking the sample. In this way, the costs of the apparatus are reduced and reliability is increased. The gas quantity reaching the sensor can be changed within narrow and reproducible limits by varying the open time of the valve. The sensor signal can increase at the start of taking the sample because of a high content of the component to be determined. If the sensor signal increases rapidly at the start, then the gas quantity reaching the sensor can be held small by an early closing of the valve. In this way, an overdrive of the sensor is avoided and the recovery time is held to a minimum. On the other hand, when the gas sample contains only a small amount of the component to be determined, the sensitivity of the detection can be increased by means of a large gas quantity in the sensor in that the open time of the valve is correspondingly extended.

The sample conduit is preferably configured as a capillary tube whereby a back diffusion of gas from the sensor is effectively prevented during the measurement when the gas flow is at standstill. The flow resistance of the capillary tube is preferably so selected that approximately one-thousandth of the volume flow flowing through the testing conduit flows through the sensor.

It is advantageous to heat the capillary tube when the apparatus is used for investigating breathing air to prevent a condensation of moisture.

The gas can be conducted over the surface of the sensor in a spiral channel in order to obtain the best possible contact of the gas with the sensor surface.

BRIEF DESCRIPTION OF THE DRAWING

The invention will now be described with respect to the single FIGURE of the drawing which shows an apparatus of the invention for determining the alcohol content of breathing air.

DESCRIPTION OF THE PREFERRED EMBODIMENTS OF THE INVENTION

The apparatus of the invention shown in the FIGURE includes a testing conduit 1 having a throttle 2. A sample conduit 3 branches from the testing conduit 1 upstream of the throttle 2 and leads to an inlet 4 of an electrochemical gas sensor 5 sensitive to alcohol. A valve 7 is connected to a gas outlet 6 of the sensor 5 and a pressure sensor 8 is connected to the sample conduit 3. An electric heater 9 acts on the sample conduit 3. A control unit 11 is connected to the following: the pressure sensor 8, the heater 9, the gas sensor 5, the valve 7 and a display unit 10.

A measurement of the alcohol content of a breath sample takes place in the manner described below.

A person (not shown) blows into the input 12 of the testing conduit 1 while the valve 7 is initially closed. The air blown in leaves the testing conduit at the output 14 thereof and flows into the ambient. A pressure builds up forward of the throttle 2 and is measured by pressure sensor 8. The control unit 11 forms the time integral of the signals of the pressure sensor and computes the gas volume therefrom which flows through the testing conduit 1. The control unit 11 takes account of the flow resistance of the throttle 2 in the computation of the gas volume. Only the so-called alveolar air which originates from the lung can be used to obtain a correct measurement. The control unit 11 therefore opens the valve 7 only after a minimum gas volume has flown through the testing conduit 1.

After the valve 7 is opened, gas also flows into the gas sensor 5 via the sample conduit 3. In this embodiment, an electrochemical sensor is used having an output signal proportional to the quantity of the converted alcohol molecules. For a measurement of concentration, the gas quantity flowing into the sensor 5 must be known. For this purpose, the control unit 11 again forms the time integral of the signals of the pressure sensor 8 and computes the gas quantity therefrom which has flowed into the sensor 5 while considering the flow resistance of the conduit 3, the sensor 5 and the valve 7. The control unit 11 closes the valve 7 again after the throughflow of a pregiven gas quantity or after a pregiven time has elapsed. The control unit 11 computes the alcohol concentration in the breath sample from the determined gas quantity and the signal of the gas sensor 5 and displays the result on the display unit 10.

The greater the alcohol content of the breath sample, the greater is the rapidity with which the signal of the gas sensor 5 increases after the valve 7 is opened.

The control unit 11 can select the valve-open time to be shorter for a rapid increase and longer for a slower increase. In this way, the total alcohol quantity reaching the gas sensor 5 can be maintained in a range favorable for the measurement.

An electrically-operated heater 9 is provided on the sample conduit 3 in order to prevent a condensation of moisture. The heater 9 heats the sample conduit 3 to approximately 34° C. The valve 7 arranged rearward of the sensor does not have to be heated because the gas is dried in the sensor 5. The sample conduit 3 is configured as a capillary tube having a diameter of approximately of 1 mm and a length of approximately 20 mm. In this way, the sample conduit 3 has the necessary flow resistance in order to limit the throughflow to approximately 1 cm$^3$/second and a gas diffusion during the measurement is effectively prevented.

A spirally-wound channel 13 is provided on the sensitive surface of the gas sensor 5 in order to bring the air sample into a contact with this sensitive surface which is as intensive as possible. When the valve 7 is opened, the air flows into the air inlet 4 of the gas sensor 5, flows through the channel 13, leaves the gas sensor 5 through the gas outlet 6 and finally flows through the valve 7 to the ambient. In the channel 13, the air comes into contact with the sensitive surface of the gas sensor 5 over a relatively long path.

A gas sensor of the kind suitable for use as the gas sensor 5 is described in U.S. Pat. No. 4,976,135 which is incorporated herein by reference. The gas sensor 5 can, for example, be a "Dräger Sensor Alcotest" (product number 68 07 220) marketed by Dräger Aktiengesellschaft of Lübeck, Germany.

It is understood that the foregoing description is that of the preferred embodiments of the invention and that various changes and modifications may be made thereto without departing from the spirit and scope of the invention as defined in the appended claims.

What is claimed is:

1. A method for making a quantitative determination of a component in a gas flow with an apparatus including: a testing conduit for conducting the gas flow therethrough; said testing conduit having a throttle formed therein for throttling said gas flow; a gas sensor for detecting the component, said gas sensor having an inlet and an outlet; a sample line having a first end branching into said testing conduit upstream of said throttle and a second end connected to said inlet of said gas sensor; a valve connected to said outlet and being switchable between an open position wherein gas flows through said sample line, said gas sensor and said valve and a closed position wherein the flow of gas through said gas sensor is interrupted; a pressure sensor connected to said sample line for measuring the pressure of said gas flow upstream of said throttle; and, a control unit for controlling said valve and for receiving signals from said sensors; a method for making a quantitative determination of said component in said gas flow, the method comprising the steps of:

switching said valve into said open position via said control unit thereby permitting gas to flow through said sample line, said gas sensor and said valve;

determining the gas volume flowing through the sample tube by computing the time integral of said signal of said pressure sensor in said control unit; and, switching said valve into said closed position after one of the following conditions is satisfied: a pregiven volume of said gas has passed into said gas sensor via said sample conduit; and, a pregiven time span has elapsed.

2. The method of claim 1, wherein said signal of said gas sensor is measured directly after said valve is opened to determine the speed at which said signal of said gas sensor increases; and, with the pregiven volume of said gas being selected to be less than greater said speed of increase is.

3. The method of claim 1, wherein said signal of said gas sensor is measured directly after said valve is opened to determine the speed at which said signal of said gas sensor increases; and, with the pregiven time span that said valve is open being selected to be inversely related to said speed of increase of said signal.

4. An apparatus for quantitatively determining a component in a gas flow, the apparatus comprising:

testing conduit for conducting the gas flow therethrough;

said testing conduit having throttle means formed therein for throttling said gas flow;

a gas sensor for detecting the component and for supplying a signal indicative of said component, said gas sensor having an inlet and an outlet;

a sample line for conducting a portion of said gas flow as a sample gas flow, said sample line having a first end branching into said testing conduit upstream of said throttle means for receiving said sample gas flow and a second end connected to said inlet of said gas sensor;

a valve connected to said outlet and being switchable between a closed position wherein a passing of said sample gas flow through said gas sensor is prevented and an open position wherein said sample gas flow can pass through said gas sensor;

a pressure sensor connected to said sample line for measuring the pressure of said gas flow upstream of said throttle means and for supplying a signal indicative of said pressure; and, control means connected to said sensors for receiving said signals, said control means also being connected to said valve for controlling said valve to switch between said positions and being adapted for making a quantitative determination of said component with the aid of said signals.

5. The apparatus of claim 4, said sample line being configured as a capillary tube; said capillary tube being dimensioned to have a flow resistance so as to permit a volumetric flow to pass therethrough corresponding to approximately 1/1000 of the volumetric flow passing through said testing conduit.

6. The apparatus of claim 5, further comprising heater means for heating said capillary tube.

7. The apparatus of claim 5, said gas sensor having a sensing surface and a spiral channel for spirally conducting said sample gas flow over said sensing surface.

* * * * *

UNITED STATES PATENT AND TRADEMARK OFFICE
CERTIFICATE OF CORRECTION

PATENT NO. : 5,321,972
DATED : June 21, 1994
INVENTOR(S) : Burkhard Stock

It is certified that error appears in the above-identified patent and that said Letters Patent is hereby corrected as shown below:

In column 4, line 17: delete "than" and substitute -- the -- therefor.

In column 4, line 27: before "testing", insert -- a --.

Signed and Sealed this

Sixth Day of September, 1994

Attest:

BRUCE LEHMAN

Attesting Officer

Commissioner of Patents and Trademarks